US011011269B2

(12) United States Patent
Dadey

(10) Patent No.: US 11,011,269 B2
(45) Date of Patent: May 18, 2021

(54) MEDICAL CLAIMS AUTO CODING SYSTEM AND METHOD

(71) Applicant: MP Cloud Technologies, Inc., Austin, TX (US)

(72) Inventor: John Dadey, Austin, TX (US)

(73) Assignee: MP Cloud Technologies, Inc., Austin, TX (US)

( * ) Notice: Subject to any disclaimer, the term of this patent is extended or adjusted under 35 U.S.C. 154(b) by 587 days.

(21) Appl. No.: 15/295,953

(22) Filed: Oct. 17, 2016

(65) Prior Publication Data

US 2017/0109485 A1    Apr. 20, 2017

Related U.S. Application Data

(60) Provisional application No. 62/242,251, filed on Oct. 15, 2015.

(51) Int. Cl.
*G16H 40/63* (2018.01)
*G06Q 40/08* (2012.01)

(52) U.S. Cl.
CPC ............ *G16H 40/63* (2018.01); *G06Q 40/08* (2013.01)

(58) Field of Classification Search
CPC combination set(s) only.
See application file for complete search history.

(56) References Cited

U.S. PATENT DOCUMENTS

| | | | |
|---|---|---|---|
| 2003/0212575 A1* | 11/2003 | Saalsaa et al. |
| 2005/0137912 A1* | 6/2005 | Rao et al. |
| 2009/0222539 A1* | 9/2009 | Lewis et al. |
| 2009/0265187 A1* | 10/2009 | Boone et al. |
| 2011/0093278 A1* | 4/2011 | Hutton |
| 2012/0099712 A1* | 4/2012 | Olivarez |
| 2012/0102559 A1* | 4/2012 | Yoshida |
| 2014/0122094 A1* | 5/2014 | Smith et al. |
| 2014/0278512 A1* | 9/2014 | Young |
| 2014/0365241 A1* | 12/2014 | Dillie et al. |
| 2015/0347697 A1* | 8/2015 | Cox |
| 2015/0363555 A1* | 12/2015 | Studsrud |
| 2016/0321404 A1* | 11/2016 | Ginsburg |
| 2016/0371447 A1* | 12/2016 | Koman |

OTHER PUBLICATIONS

U.S. Appl. No. 61/590,330, filed Jan. 2012, Chaudhri et al.*

* cited by examiner

*Primary Examiner* — Michael Tomaszewski
*Assistant Examiner* — William T. Monticello
(74) *Attorney, Agent, or Firm* — Shah IP Law, PLLC

(57) ABSTRACT

A system and method for automatic coding of medical claims, so as to minimize or eliminate possible human error and oversight that is common with prior art solutions.

16 Claims, 9 Drawing Sheets

MEDICAL CLAIMS AUTO CODING SYSTEM AND METHOD

TECHNICAL FIELD

This application claims priority to and the benefit of U.S. Provisional Patent Application No. 62/242,251 filed Oct. 15, 2015, which is incorporated herein by reference in its entirety.

TECHNICAL FIELD

The subject matter described herein relates to computer-implemented claims processing for medical services, and more particularly to a system and method for auto coding of medical claims.

BACKGROUND

Medical services are often rendered by personnel that are dispatched to a location of patient, rather than initially at a hospital, in an emergency response system. Such services are typically rendered by Emergency Medical Technicians (EMTs), who are the backbone of the emergency response system. Their skills and abilities are essential to a positive medical outcome. Fire department career personnel and nearly all volunteer fire personnel are trained to at least the EMT level.

Every EMT is trained to provide basic life support (BLS). The BLS system is comprised of EMTs who have completed more than 300 hours of both classroom and practical education in trauma care, cardiac and stroke care, CPR, advanced first aid, child birth and basic medication administration. In certain cases, an advanced level of emergency care is required. ALS is an acronym for advanced life support. The ALS system is comprised of paramedics who have received more than 3,000 hours of training in aggressive cardiac life support, pediatric life support, severe trauma and more than 200 other life-threatening emergency medical conditions.

Medical services that are rendered to a patient outside of a hospital, such as ALS or BLS, are typically covered at least in part by an insurance plan. An insurer, whether it is a government entity or private entity, will pay at least some of the costs of these medical services. Some challenges with payments by an insurer include the documentation required and the proper designation or classification of medical services. Insurers require precise documentation of the rendering of medical services in order to adequately cover their agreed-upon costs per the insurance plan. In an environment other than a hospital, such document is very difficult to obtain, let alone be precise.

While computer-implemented documentation systems have been introduced to automate the enormous task of processing medical claims, such systems still rely on human input, and are still subject to human error and oversight.

SUMMARY

In one aspect, an auto coding system and method are presented, in which a computer processor automatically encodes a medical claim for precise processing and settlement of the medical claim by medical payment entity such as an insurer.

The auto coding system and method executes the steps of generating an electronic claim for an emergency medical services event. The electronic claim includes a number of data fields that describe at least one or more service providers, a dispatch reason, a treatment rendered, a destination type, and a level of emergency related to the emergency medical services event. The system and method further include accessing, via a communications network, a national emergency medical services information system (NEMSIS) database, and retrieving from the NEMSIS database a set of billing codes corresponding to at least one of the data fields. Each billing code of the set of billing codes having a billing rate related to one of the at least one or more service providers, the dispatch reason, the treatment rendered, the destination type, or the level of emergency. The system and method further includes generating a graphical user interface of the electronic claim and including the set of billing codes, the graphical user interface for display in a graphical display. The system and method further includes providing a user input window in the graphical user interface for receiving user input to adjust any of the set of billing codes or the plurality of data fields.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference characters denote similar structures, features, or elements.

DETAILED DESCRIPTION

This document describes a system and method for automatic coding of medical claims, so as to minimize or eliminate possible human error and oversight that is common with prior art solutions.

Figure 1:
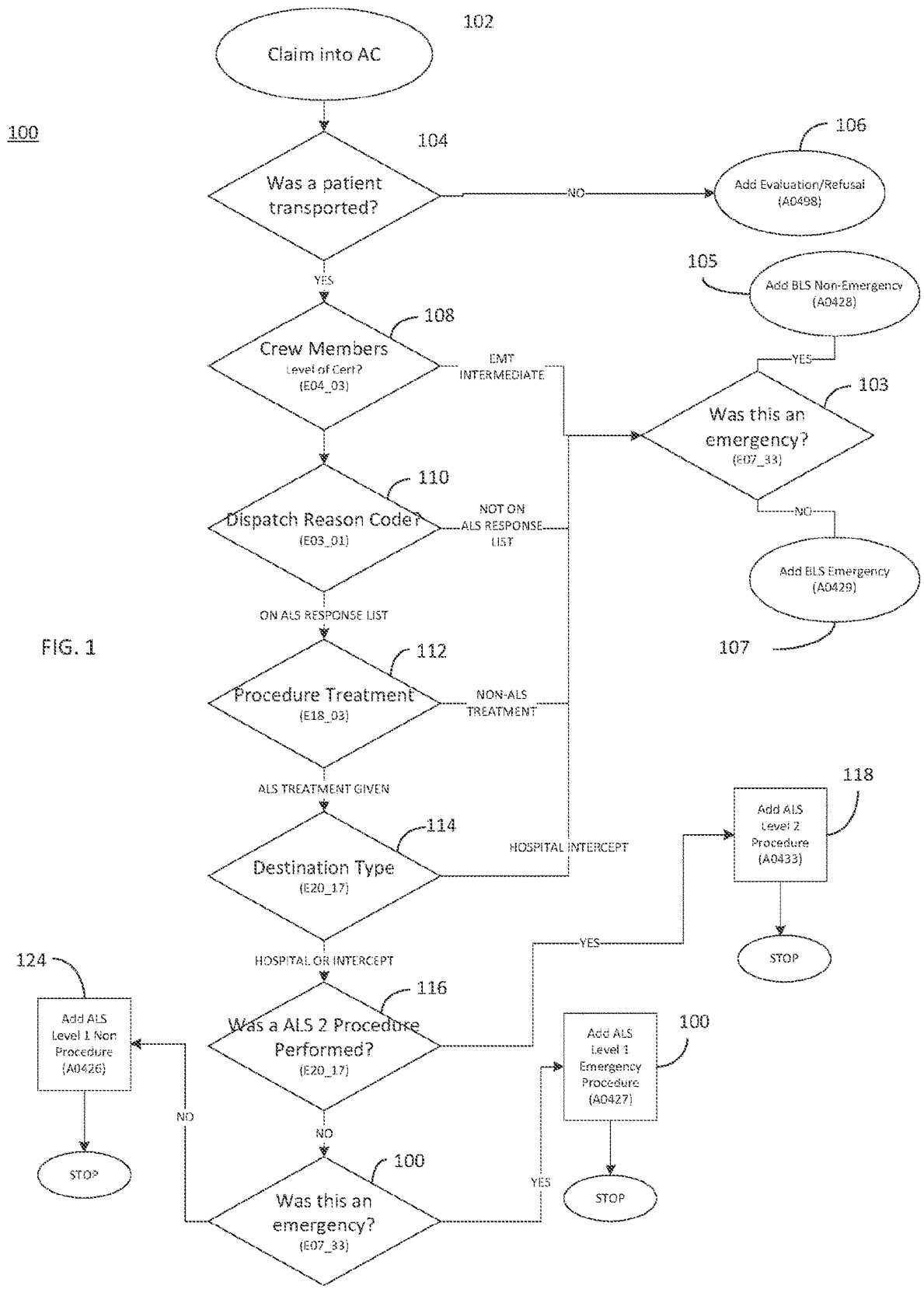
FIG. 1 is a flowchart of a level of service (LOS) workflow for medical services.

FIG. 1 is a flowchart of a level of service (LOS) workflow for medical services, as executed by an auto coding system and method. The workflow begins with uploading of a claim into a computer-implemented claims processing system. The workflow provides various prompts in a computer-generated user interface, but then reads and captures a number of fields automatically to characterize, designate, or classify medical services that have been rendered by a medical services provider to a patient. An auto coding system and method then executes logic to automatically apply procedure codes, medical necessity selections, and ICD-9 codes as needed to the respective claim. Based on the results of the auto coding, the system and method also applies of a number of system flags and makes a "Review Auto Code" button or control available in the computer-generated user interface. Accordingly, the medical claim is expeditiously and accurately populated with the proper coding for fast and accurate processing.

As an example, referring again to FIG. 1, an automated billing system and method are described, which automatically code emergency response trips based on National EMS (Emergency Medical Services) Information System (NEMSIS) data points, minimizing manpower, time, and human error. At 102, the system receives a NEMSIS file as a billing claim. The NEMSIS file can be an .xml file, and can be imported to the system by a user using a client computer, i.e. employing an RMX import. The system automatically generates a claim, and then reads and imports to the claim a number of NEMSIS fields, such as E02_18 (water circulating cold pump with pad), and other codes for first responder services.

The system can further prompt the user, at 104, whether the patient was transported in an emergency medical services (EMS) vehicle. If no, then at 106 the system can receive an evaluation and a reason for refusal to transport (per NEMSIS code A0498, for instance). If the patient was transported, the system automatically receives: the level of certification of the crew members of the EMS vehicle, per NEMSIS code E03_01 (step 108), and a dispatch reason, such as per NEMSIS code E03_01 (step 110); a procedure treatment, such as per NEMIS code E18_03 (step 112); and a destination type, such as per NEMSIS code E20_17 (step 114). The destination type can include a hospital or other destination.

The system captures the values for the above fields and uses those values to run auto coding logic. For instance, the system then applies Procedure Codes, Medical Necessity Selections, and ICD-9 codes as needed to the respective claim. At this point, a user should be able to navigate to the claim and see the applied Medical Necessity Selections, Procedure Codes and ICD-9 Codes.

If the level of certification of the crew members is designated as intermediate or below per step 108, or the reason code is not on the ALS response list, per step 110, or the procedure treatment is a non-ALS treatment, per step 112, or the destination can be classified as "hospital intercept" as per step 114, then the system determines whether the claim is directed to an emergency, at 103. If no, at 103 then the system will add a BLS non-emergency code, i.e. NEMSIS code A0428. If yes, then the system will add the BLS emergency code to the claim, i.e. NEMSIS code A0429.

After step 114, at 116 the system determines whether or not an ALS 2 procedure was performed, i.e. per NEMSIS code E20_17. If yes, at 118 the system will add into the claim a Level 2 Procedure designation (A0433), and the process stops. If no, at 120 the system queries whether the procedure was an emergency, per NEMSIS code E07_33, for instance. If yes, the system adds an ALS Level 1 emergency procedure designation to the claim, at 122. If no, the system adds an ALS Level 1 non-emergency designation to the claim, at 124. Accordingly, the electronic record of the claim will be complete, stored, and ready for transmission to an insurance company or other payee on the claim.

The system and method simplifies claims coding and produce ready-to-bill claims with one-click NEMSIS ePCR import, and achieves greater productivity with batch upload of claims. Batch posting allows for the bulk upload of 835/ERA files into a medical services claim processing system such as AdvanceClaim by Medapoint of Austin Tex., for example, for one-click payment posting. This process also automatically streamlines the creation of secondary, subsequent invoices.

The system and method further automates and manages processes with a rules-based protocol, which provides the framework for other system functions from a user worklist assignment module, where managers can intelligently manage staff and assignments; to an automated PCS processing module, where the full PCS request-submission and billing workflow is automated; to the auto code module of the present disclosure, where a medical services trip is automatically coded based on NEMSIS data points.

In accordance with implementations described herein, each trip is automatically coded. The solution is ICD-10 compliant and programmed according to Medicare-defined rules that ensure payment on claims. The trip is auto-imported into a medical services claim processing system such as AdvanceClaim, which analyzes the NEMSIS data points upon which the coding is based, and then accordingly adds procedure codes for the determined level of service and mileage, along with additional medical necessity items. The system generates results in a graphical user interface, which can be reviewed before submitting the "touchless claim" for processing. These features minimize manpower and human error.

Based on the results of auto coding, the system also applies one of the following system flags and makes the 'Review Auto Code' button available:

"Not_Coded"—when none of the above mentioned fields are available upon import.

"Partially_Coded"—when at least one of the above mentioned fields are available for auto coding.

"Auto_Coded"—when all of the above mentioned fields are available.

Figure 2:
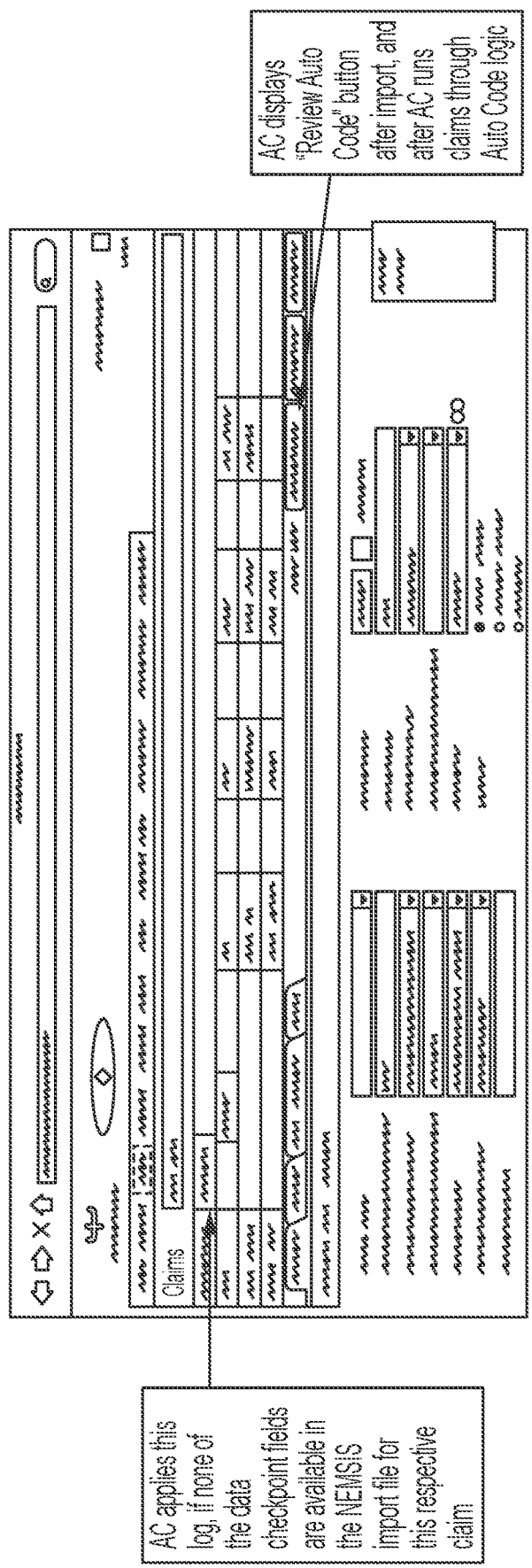
FIGS. 2-4 show a graphical user interface for displaying information about one or more data fields.
Figure 3:
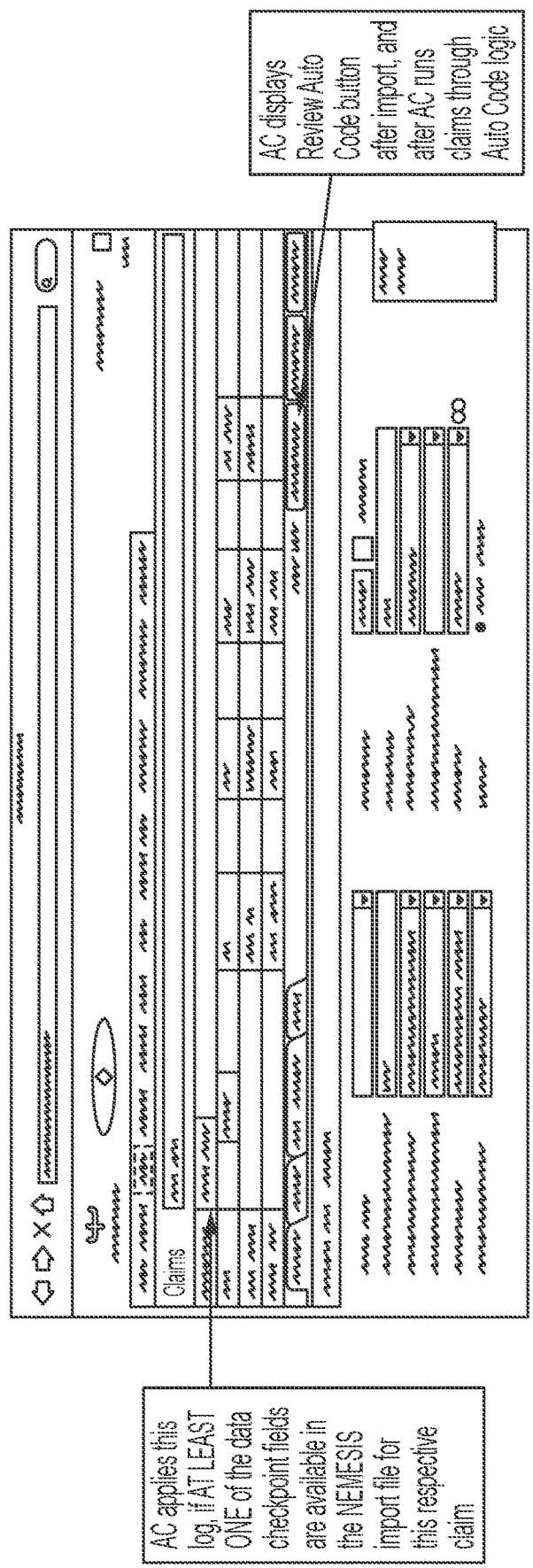
Figure 4:
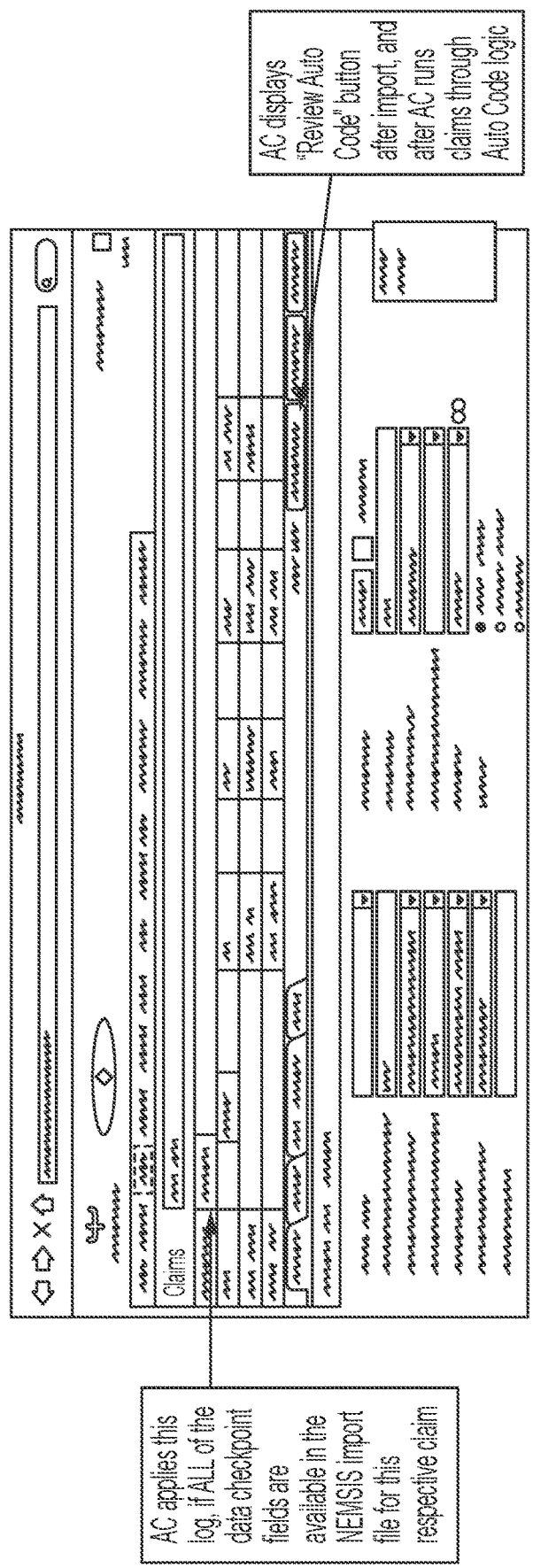

In further detail, the system applies one of the following system flags and makes the 'Review Auto Code' button available in a user interface. The user can select a button or pull-down menu representing a "Not Coded" option when none of the above mentioned fields are available upon import, as shown in FIG. 2, or can select a button or pull-down menu representing a "Partially Coded" option when at least one of the above mentioned fields are available for auto coding, as shown in FIG. 3. Finally, the user can select a button representing an "Auto Coded" when all of the above mentioned fields are available for auto coding, as shown in FIG. 4.

Figure 5:
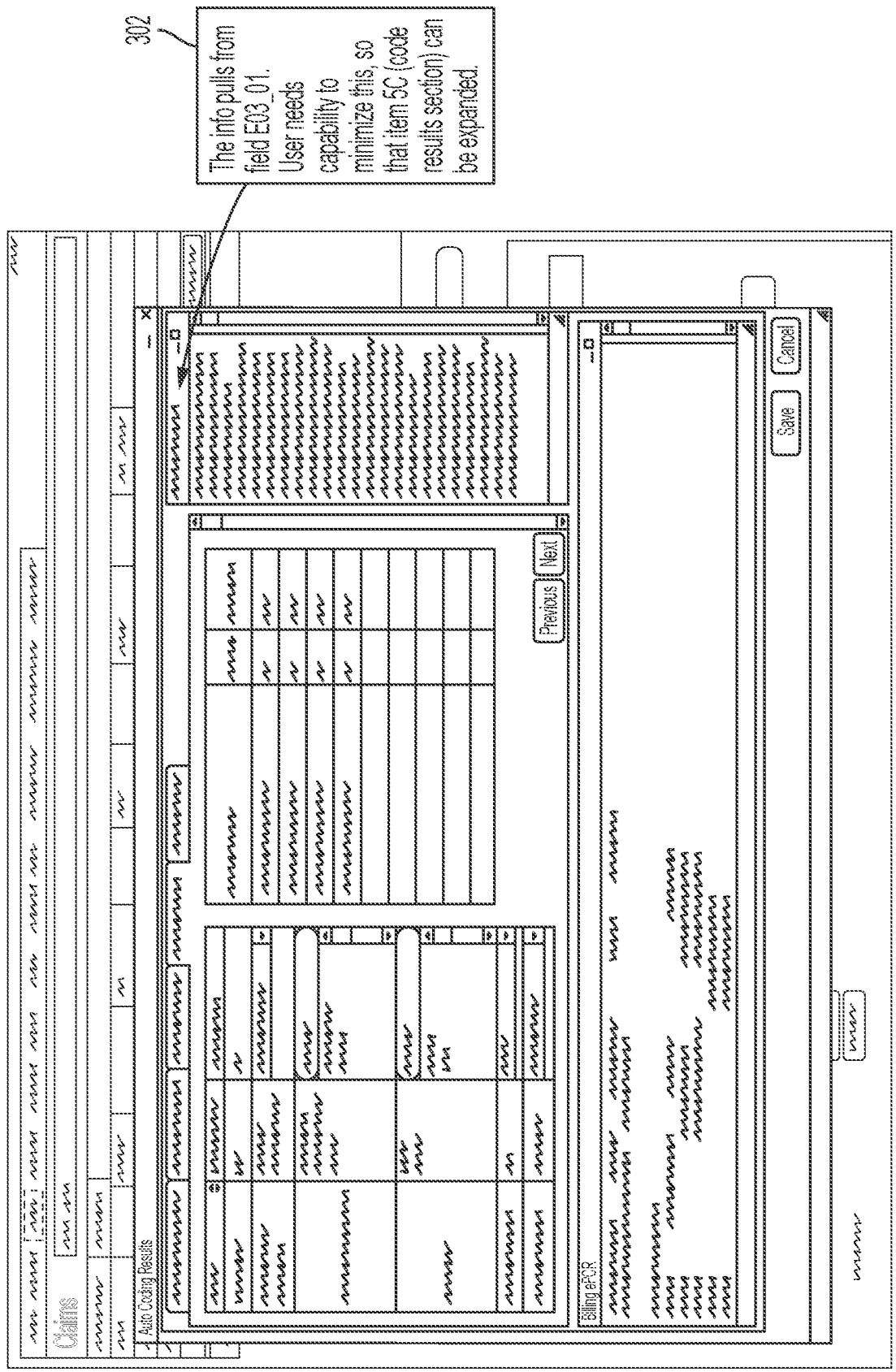
FIGS. 5-9 show a graphical user interface for automatically encoding one or more data fields related to an emergency medical services event and trip associated with the rendering of emergency medical services.

FIGS. 5-9 illustrate a graphical user interface (GUI) 300 of an auto coding system in accordance with some implementations. The GUI 300 of the auto coding system provides one or more buttons or other user-selectable graphics, to enable a user to review the auto coding. In some implementations, a first window or region 302 of the GUI, as shown in FIG. 5 is generated and presented so that the user can select a "Review Auto Code" button, and an "Auto Coding Results" window or pop up is displayed to provide a NEMSIS narrative. This section of the pop up will pull info, i.e. from NEMSIS field E13_01. This section also has the capability to be minimized so another item can be expanded in its place.

Figure 6:
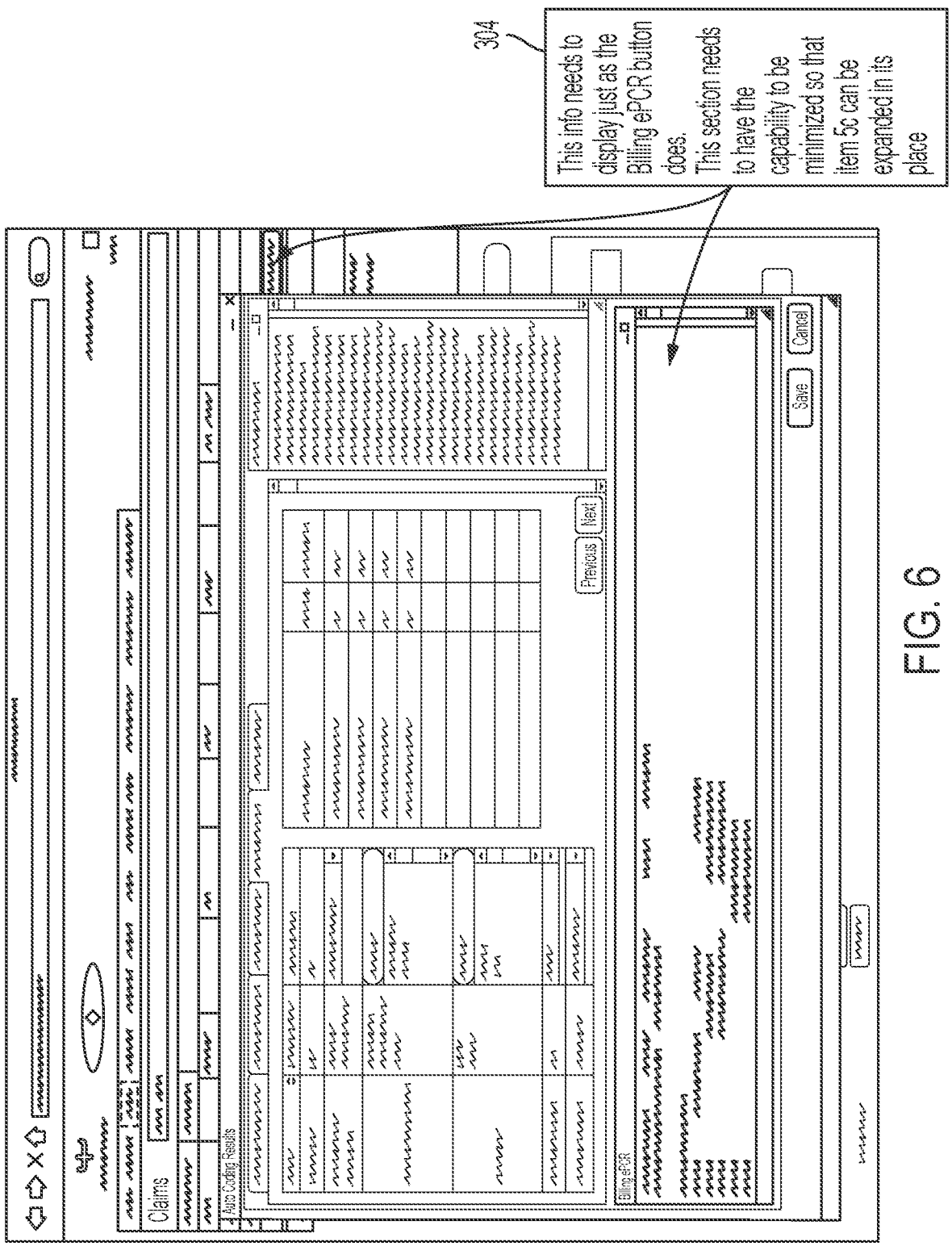

A second window or region 304, represented in FIG. 6, shows a "billing ePCR" page. This portion of the GUI will display info just as a Billing ePCR button on the claim as generated by the system. This page also has the capability to be minimized so that another section can be expanded in its place.

Figure 7:
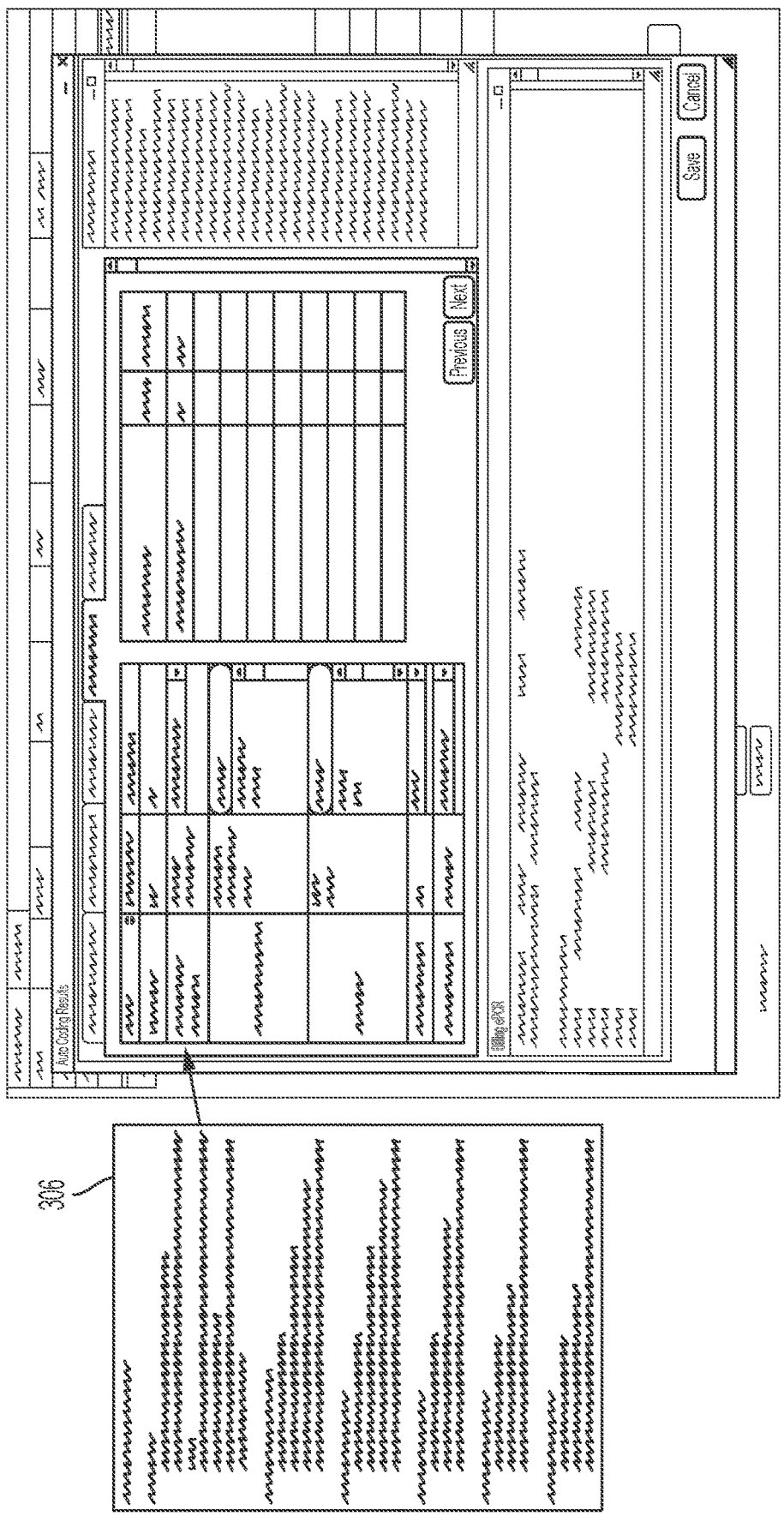

A third window or region 306 of the GUI, as shown in FIG. 7, enables display of imported information, user selections, and auto code results. For imported information, the page can display values that came in through the NEMSIS file. If a field (except for loaded miles) comes in with a value of −5, −10, or −25 then the NEMSIS value column will read N/A.

In a preferred exemplary implementation, the following information can be displayed in the third window or region 306 of the GUI Loaded Miles:
This value pulls from fields E02_17 & E02_18
The value of E02_18 subtracted from the value in E02_17 gets loaded in here.
IF E02_17 value is equal to −5, −25, or −10 treat that as 0 value when completing the above calculation.
IF E02_18 value is equal to −5, −25, or −10 THEN the NEMSIS Value Loaded Miles will be N/A
Crew Member Level of Cert:
This pulls from field E04_03.
There may be multiple entries for field E04_03.
See data dictionary for what values relate to what selection.
If this field is filled with −5, −10, or −25 THEN field is filled with N/A.
Dispatch Reason Code:
This pulls from field E03_01.
There may be multiple E03_01 entries for this field.
See data dictionary for what values relate to what selection.
If this field is filled with −5, −10, or −25 THEN field is filled with N/A .
Procedure/Intervention:
This pulls from field E18_03
This will be a string value that will come in this field.
If this field is filled with −5, −10, or −25 THEN field is filled with N/A.
Destination Type:
This pulls from field E20_17.
There will only be one value in this field.
If this field is filled with −5, −10, or −25 THEN field is filled with N/A.
Response Urgency:
This pulls from field E07_33.
There will only be one value in this field.
If this field is filled with −5, −10, or −25 THEN field is filled with N/A.

Figure 8:
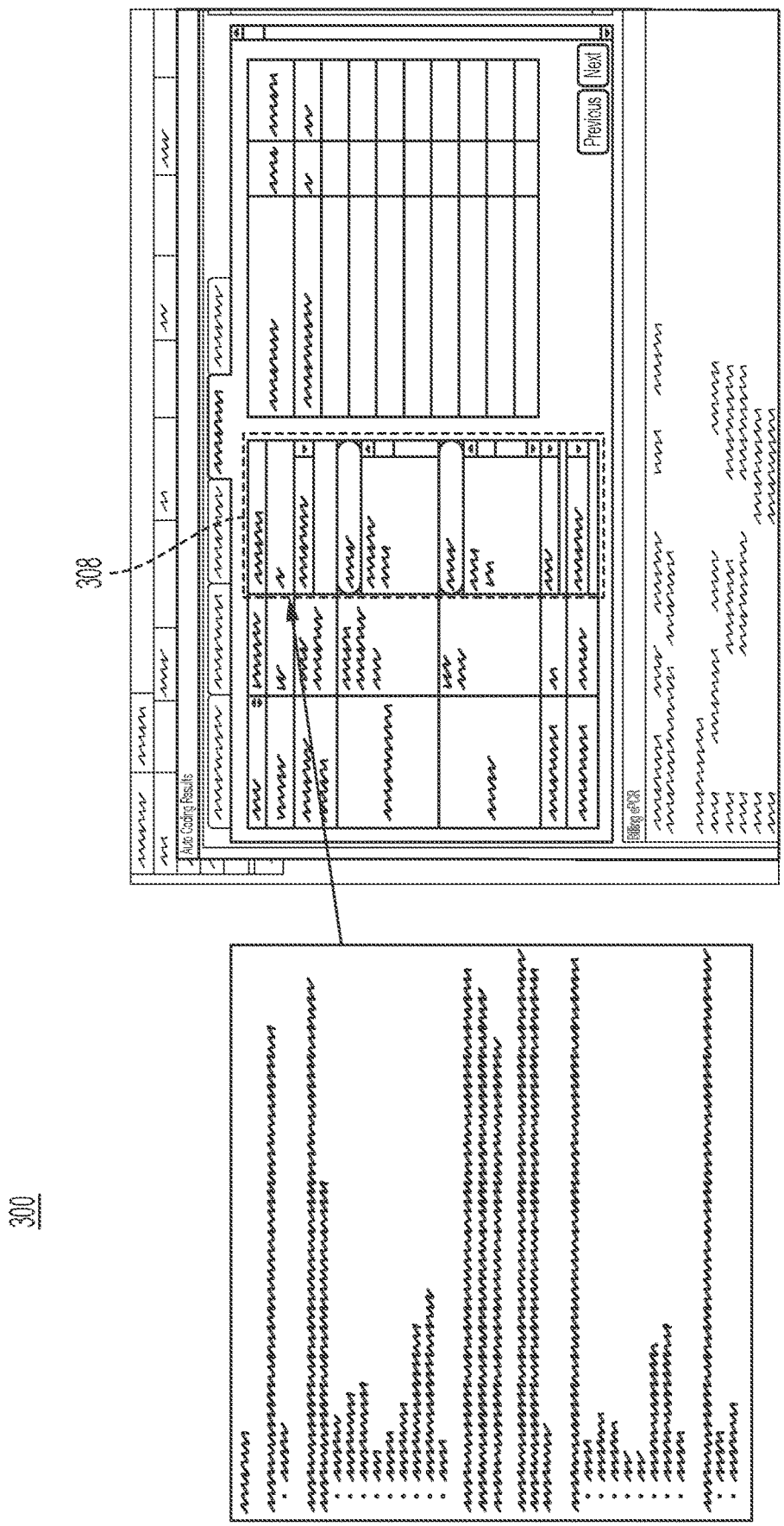
Figure 9:
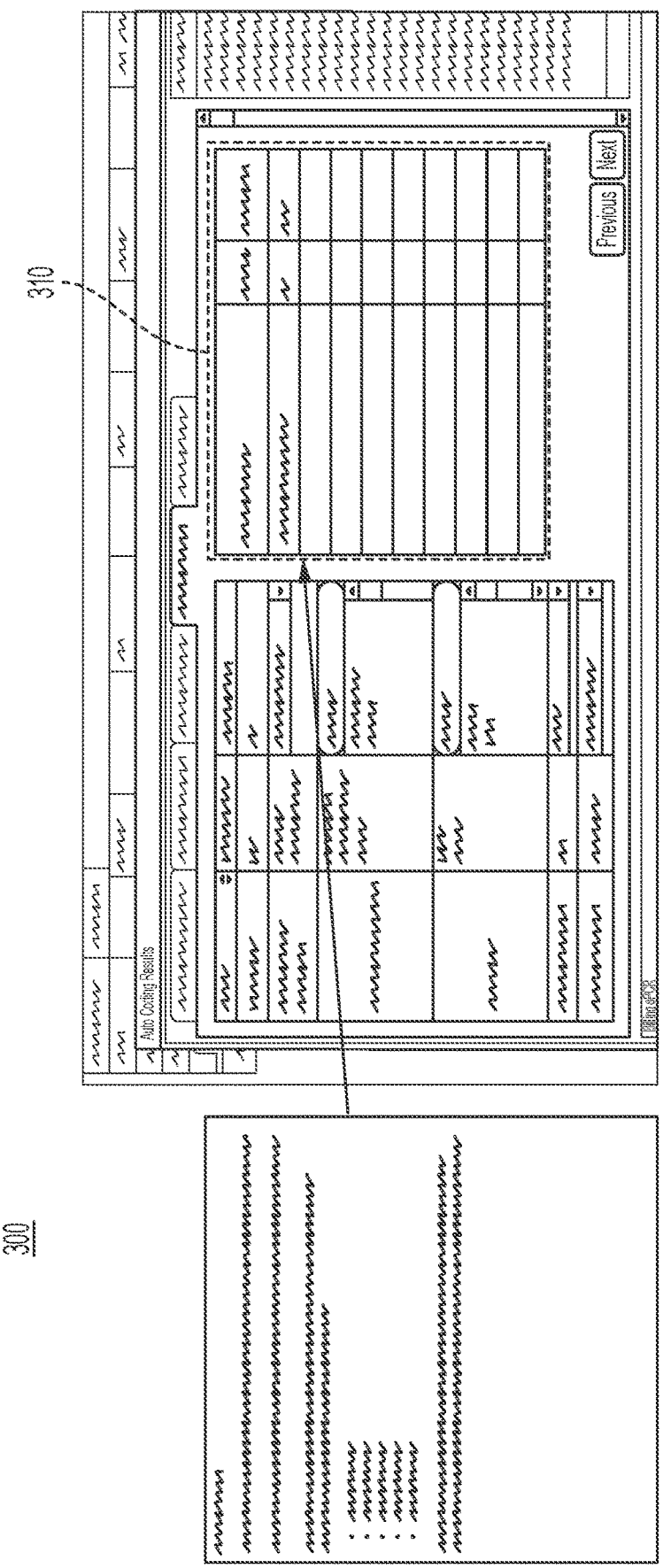

The user selection section allows a user to be able to load in values for each of the six data points described above. If a user selection value is loaded in a fourth window or region 308, it overrides the data that was received via NEMSIS, as shown in FIG. 8. Each data point can be selected by the user as described below:

Loaded Miles—A Text box that can be filled ONLY with an INT value. It can include decimal places.
Ie. 4.0 or 4
Crew Members Level of Cert—This will be a drop down list containing the following items IN THE BELOW ORDER. The user also needs to be able to select and add multiple.
EMT—Basic
EMT—Paramedic
EMT—Intermediate
Nurse
Physician
First Responder
Other Health Care Professional
Other Non-Health Care Professional
Student
Dispatch Reason Code—This is going to be a live search box that searches against the Admin Setup Dispatch Reason Codes. (See data dictionary.) This live search box should work similar to how adding a payer to a patients record works. User needs to be able to add multiple Dispatch Reason Codes if needed.
Interventions—This will have the same search and add capability as the dispatch reason codes mentioned above. This is a live search box against the Admin Setup Interventions List. User needs to be able to search and add multiple if needed.
Destination Type—This will be a drop down list of the below items. User only needs the capability to select one.
Hospital
Nursing Home
Medic/Clinic
Home
Other
Other EMS Responder(Air)
Other EMS Responder(Ground)
Police/Jail
Response Urgency—This will be a drop down list of the below items. User only needs the capability to select one.
Emergency
Non-Emergency If a user makes a user selection, then this new inputted value is used, and the data is run through the auto code logic of the auto code system, as shown in FIG. 9. A fifth window or region 310 of the GUI 300 displays the list of results generated from the auto code logic. For Procedure Codes, this includes adding the Procedure Codes to the claim. The confidence rating is calculated based on how many of the data checkpoint fields were available upon import. If a user adds in a field via the user selection option, then the system updates the confidence rating if it was previously not available upon import.

The updated electronic claim can be included in an ePCR file, and transmitted electronically, via a communications network, to a medical payor computer for payment of the claim to the EMS provider or the like.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
obtaining, by a computer processor of an auto coding system, a plurality of national emergency medical services information system (NEMSIS) files from a plurality of computing devices in communication via a communications network, individual NEMSIS files comprising data corresponding to respective emergency medical services events;
receiving patient information identifying a patient;
selecting a NEMSIS file from the plurality of NEMSIS files for the patient based on an emergency medical services event;
generating, by the computer processor, an electronic claim in response to obtaining the NEMSIS file;
automatically updating, by the computer processor, the electronic claim to generate an updated electronic claim by importing into the electronic claim relevant data from the NEMSIS file;
identifying computer-readable information that relates at least procedure codes, medical necessity selection codes, and diagnosis codes with the relevant data in the updated electronic claim;
automatically completing, by the computer processor, the updated electronic claim to generate a completed electronic claim by applying auto coding logic, the auto coding logic using the computer-readable information to retrieve one of the procedure codes, the medical necessity selection codes, or the diagnosis codes that are applicable to the relevant data in the updated electronic claim;
applying a system flag to at least one field of a plurality of fields represented in the updated electronic claim based on availability of retrieved procedure codes, medical necessity selection codes, diagnosis codes for individual fields of the plurality of fields, the system flag indicating a status of a field, the status indicating one of no fields being available for import, at least one field being available for import, or the plurality of fields being available for import;
generating, by the computer processor, a graphical user interface of the completed electronic claim and the system flag to the at least one field, the graphical user interface for display by a graphical display;
providing, by the computer processor, a user input window in the graphical user interface for receiving first user input to adjust one or more values in the completed electronic claim based on at least the system flag to generate adjusted values;
automatically finalizing, by the computer processor, the completed electronic claim to generate a finalized electronic claim, the finalized electronic claim generated by re-applying auto coding logic to the adjusted values if a value in the completed electronic claim is adjusted by the first user input;

providing, by the computer processor, a graphical user interface for receiving second user input to submit a finalized electronic claim form that includes information for the finalized electronic claim; and submitting the finalized electronic claim form to initiate payment process for the emergency medical services event.

2. The method in accordance with claim 1, wherein one or more procedure codes, medical necessity selection codes, or diagnosis codes are selected in accordance with payment guidelines provided by a payor for one or more treatments and/or one or more services rendered during the emergency medical services event.

3. The method in accordance with claim 2, further comprising generating, by the computer processor, an electronic patient care reporting (ePCR) file including the finalized electronic claim.

4. The method in accordance with claim 3, further comprising transmitting, by the computer processor, the ePCR file via a communications network to a medical payor computer.

5. A non-transitory computer program product storing instructions that, when executed by at least one programmable processor of an auto coding system, cause the at least one programmable processor to perform operations comprising:

obtain a plurality of national emergency medical services information system (NEMSIS) files from a plurality of computing devices in communication via a communications network, individual NEMSIS files comprising data corresponding to respective emergency medical services events;

receive patient information identifying a patient;

select a NEMSIS file from the plurality of NEMSIS files for the patient based on an emergency medical services event generate an electronic claim in response to obtaining the NEMSIS file;

automatically update the electronic claim to generate an updated electronic claim by importing into the electronic claim relevant data from the NEMSIS file;

identify computer-readable information that relates at least procedure codes, medical necessity selection codes, and diagnosis codes with the relevant data in the updated electronic claim;

automatically complete the updated electronic claim to generate a completed electronic claim by applying auto coding logic, the auto coding logic using the computer-readable information to retrieve one of the procedure codes, the medical necessity selection codes, or the diagnosis codes that are applicable to the relevant data in the updated electronic claim;

apply a system flag to at least one field of a plurality of fields represented in the updated electronic claim based on availability of retrieved procedure codes, medical necessity selection codes, diagnosis codes for individual fields of the plurality of fields, the system flag indicating a status of a field, the status indicating one of no fields being available for import, at least one field being available for import, or the plurality of fields being available for import;

generate a graphical user interface of the completed electronic claim and the system flag to the at least one field, the graphical user interface for display by a graphical display;

provide a user input window in the graphical user interface for receiving first user input to adjust one or more values in the completed electronic claim based on at least the system flag to generate adjusted values;

automatically finalize the completed electronic claim to generate a finalized electronic claim, the finalized electronic claim generated by re-applying auto coding logic to the adjusted values if a value in the completed electronic claim is adjusted by the first user input;

provide a graphical user interface for receiving user input to submit a finalized electronic claim form that includes information for the finalized electronic claim; and submit the finalized electronic claim form to initiate payment process for the emergency medical services event.

6. The non-transitory computer program product in accordance with claim 5, wherein the procedure codes, medical necessity selection codes, and/or diagnosis codes are selected in accordance with payment guidelines provided by a payor for one or more treatments and/or one or more services rendered during the emergency medical services event.

7. The non-transitory computer program product in accordance with claim 6, wherein the operations further comprise generating an electronic patient care reporting (ePCR) file including the finalized electronic claim.

8. The non-transitory computer program product in accordance with claim 7, wherein the operations further comprise transmitting the ePCR file via a communications network to a medical payorcomputer.

9. Asystem comprising:

at least one programmable processor; and a machine-readable medium storing instructions that, when executed by the at least one programmable processor, cause the at least one programmable processor to perform operations comprising:

obtain a plurality of national emergency medical services information system (NEMSIS) files from a plurality of computing devices in communication via a communications network, individual NEMSIS files comprising data corresponding to respective emergency medical services events;

receive patient information identifying a patient;

select a NEMSIS file from the plurality of NEMSIS files for the patient based on an emergency medical services event generate an electronic claim in response to obtaining the NEMSIS file;

automatically update the electronic claim to generate an updated electronic claim by importing into the electronic claim relevant data from the NEMSIS file;

identify computer-readable information that relates at least procedure codes, medical necessity selection codes, and diagnosis codes with the relevant data in the updated electronic claim;

automatically complete the updated electronic claim to generate a completed electronic claim by applying auto coding logic, the auto coding logic using the computer-readable information to retrieve one of the procedure codes, the medical necessity selection codes, or the diagnosis codes that are applicable to the relevant data in the updated electronic claim;

apply a system flag to at least one field of a plurality of fields represented in the updated electronic claim based on availability of retrieved procedure codes, medical necessity selection codes, diagnosis codes for individual fields of the plurality of fields, the system flag indicating a status of a field, the status indicating one of no fields being available for import, at least one field being available for import, or the plurality of fields being available for import;

generate a graphical user interface of the completed electronic claim and the system flag to the at least one field, the graphical user interface for display by a graphical display;

provide a user input window in the graphical user interface for receiving first user input to adjust one or more values in the completed electronic claim based on at least the system flag to generate adjusted values;

automatically finalize the completed electronic claim to generate a finalized electronic claim, the finalized electronic claim generated by re-applying auto coding logic to the adjusted values if a value in the completed electronic claim is adjusted by the first user input;

provide a graphical user interface for receiving user input to submit a finalized electronic claim form that includes information for the finalized electronic claim; and submit the finalized electronic claim form to initiate payment process for the emergency medical services event.

10. The system in accordance with claim 9, wherein the procedure codes, medical necessity selection codes, and/or diagnosis codes are selected in accordance with payment guidelines provided by a payor for one or more treatments and/or one or more services rendered during the emergency medical services event.

11. The system in accordance with claim 10, wherein the operations further comprise generating an electronic patient care reporting (ePCR) file including the finalized electronic claim.

12. The system in accordance with claim 11, wherein the operations further comprise transmitting the ePCR file via a communications network to a medical payor computer.

13. The method in accordance with claim 1, wherein the auto coding logic identifies a level of emergency based on data in the NEMSIS file.

14. The method in accordance with claim 13, wherein the auto coding logic applies a basic life support (BLS) non-emergency code if the level of certification of crew members processing the emergency medical services event is designated as intermediate, or a reason code is not in an advanced life support (ALS) response list, or a procedure treatment is a non-ALS treatment, or if a destination can be classified as a hospital intercept.

15. The method in accordance with claim 13, wherein the auto coding logic applies an advanced life support level one (ALS-1) code based on data in the NEMSIS file.

16. The method in accordance with claim 13, wherein the auto coding logic applies an advanced life support level two (ALS-2) code based on data in the NEMSIS file.

* * * * *